(12) United States Patent
Garcon et al.

(10) Patent No.: US 6,846,489 B1
(45) Date of Patent: Jan. 25, 2005

(54) VACCINES CONTAINING A SAPONIN AND A STEROL

(75) Inventors: Nathalie Marie-Josephe Claude Garcon, Wavre (BE); Martin Friede, Brussels (BE)

(73) Assignee: SmithKline Beecham Biologicals s.a., Rixensart (BE)

( * ) Notice: Subject to any disclaimer, the term of this patent is extended or adjusted under 35 U.S.C. 154(b) by 0 days.

(21) Appl. No.: 09/478,705

(22) Filed: Jan. 6, 2000

Related U.S. Application Data

(62) Division of application No. 09/102,676, filed on Jun. 23, 1998, now abandoned, which is a division of application No. 08/945,450, filed as application No. PCT/EP96/01464 on Apr. 1, 1996, now abandoned.

(30) Foreign Application Priority Data

Apr. 25, 1995 (GB) .............................................. 9508326
Jun. 28, 1995 (GB) .............................................. 9513107

(51) Int. Cl.$^7$ ............................................. A61K 45/00
(52) U.S. Cl. ................................... 424/278.1; 514/1.21
(58) Field of Search ....................... 424/278.1; 514/1.21

(56) References Cited

U.S. PATENT DOCUMENTS 5,750,110 A * 5/1998 Prieels et al. ............ 424/208.1

FOREIGN PATENT DOCUMENTS

WO          WO 94/00153       *   1/1994

OTHER PUBLICATIONS

Mueller, N., 1995, "Overview: Viral Agents and Cancer", Environ. Health Perspect. 103(S8):259–261.*
Özel, M., et al., 1989, "Quaternary Structure of the Immunostimulating Complex (ISCOM)" J. Ultra. Molec. Struc. Res. 102:240–248.*
Gupta, R.K. et al., 1993, "Adjuvants–a balance between toxicity and adjuvanticity", Vaccine 11(3):293–306.*

* cited by examiner

*Primary Examiner*—Laurie Scheiner
*Assistant Examiner*—Jeffrey S. Parkin
(74) *Attorney, Agent, or Firm*—Jeffrey A. Sutton; Stephen Venetianer; Charles M. Kinzig

(57) ABSTRACT

A novel adjuvant composition comprising a sterol (e.g., cholesterol, β-sitosterol, stigmasterol, ergosterol, and ergocalciferol) and saponin fraction (e.g., QS21, also known as QA21) in the form of an immunostimulating complex, or ISCOM, is disclosed. QS21 is an immunologically active saponin fraction having adjuvant activity derived from the bark of Quillaja Saponaria Molina. Previous attempts in the prior art to prepare ISCOMs comprising QS21 were unsuccessful. Thus, the instant application discloses the first successful attempt to prepare ISCOMs comprising purified QS21. Small unilamelar liposomes containing cholesterol, in the absence of any detergent, were prepared, followed by the addition of an aqueous solution of QS21. The claimed compositions will prove useful in the preparation of highly immunogenic vaccine compositions.

4 Claims, 4 Drawing Sheets

VACCINES CONTAINING A SAPONIN AND A STEROL

This is a divisional of application Ser. No. 09/102,676 filed Jun. 23, 1998 abn; which is a division of application Ser. No. 08/945,450 filed Dec. 12, 1997 abn which is a 371 of application Ser. No. PCT/EP96/01464 filed Apr. 1, 1996; which claims priority to Foreign Application Nos. GB 9508326.7 filed Apr. 25, 1995 and GB 9513107.4 filed Jun. 28, 1995.

The present invention relates to novel vaccine formulations, to methods of their production and to their use in medicine. In particular, the present invention relates to vaccines containing an antigen, an immunologically active fraction derived from the bark of Quillaja Saponaria Molina such as QS21, and a sterol.

Immunologically active saponin fractions having adjuvant activity derived from the bark of the South American tree Quillaja Saponaria Molina are known in the art. For example QS21, also known as QA21, an Hplc purified fraction from the Quillaja Saponaria Molina tree and it's method of its production is disclosed (as QA21) in U.S. Pat. No. 5,057,540. Quillaia saponin has also been disclosed as an adjuvant by Scott et al, Int. Archs. Allergy Appl. Immun., 1985, 77, 409. However, the use of QS21 as an adjuvant is associated with certain disadvantages. For example when QS21 is injected into a mammal as a free molecule it has been observed that necrosis, that is to say, localised tissue death, occurs at the injection site.

It has now surprisingly been found that necrosis at the injection site can be avoided by use of formulations containing a combination of QS21 and a sterol. Preferred sterols include β-sitosterol, stigmasterol, ergosterol, ergocalciferol and cholesterol. These sterols are well known in the art, for example cholesterol is disclosed in the Merck Index, 11th Edn., page 341, as a naturally occuring sterol found in animal fat.

In a first aspect the present invention therefore provides a vaccine composition comprising an antigen, an immunologically active saponin fraction and a sterol. Preferably the compositions of the invention contain the immunologically active saponin fraction in substantially pure form. Preferably the compositions of the invention contain QS21 in substantially pure form, that is to say, the QS21 is at least 90% pure, preferably at least 95% pure and most preferably at least 98% pure. Other immunologically active saponin fractions useful in compositions of the invention include QA17/QS17. Compositions of the invention comprising QS21 and cholesterol show decreased reactogenicity when compared to compositions in which the cholesterol is absent, while the adjuvant effect is maintained In addition it is known that QS21 degrades under basic conditions where the pH is about 7 or greater. A further advantage of the present compositions is that the stability of QS21 to base-mediated hydrolysis is enhanced in formulations containing cholesterol.

Preferred compositions of the invention are those forming a liposome structure. Compositions where the sterol/immunologically active saponin fraction forms an ISCOM structure also form an aspect of the invention.

The ratio of QS21: sterol will typically be in the order of 1:100 to 1:1 weight to weight. Preferably excess sterol is present, the ratio of QS21: sterol being at least 1:2 w/w.

Typically for human administration QS21 and sterol, will be present in a vaccine in the range of about 1 μg to about 100 μg, preferably about 10 g to about 50 μg per dose.

The liposomes preferably contain a neutral lipid, for example phosphatidylcholine, which is preferably non crystalline at room temperature, for example eggyolk phosphatidylcholine, dioleoyl phosphatidylcholine or dilauryl phosphatidylcholine. The liposomes may also contain a charged lipid which increases the stability of the lipsome-QS21 structure for liposomes composed of saturated lipids. In these cases the amount of charged lipid is preferably 1–20% w/w, most preferably 5–10%. The ratio of sterol to phospholipid is 1–50% (mol/mol), most preferably 20–25%.

Preferably the compositions of the invention contain MPL (3-deacylated monophosphoryl lipid A, also known as 3D-MPL). 3D-MPL is known from GB 2 220 211 (Ribi) as a mixture of 3 types of De-O-acylated monophosphoryl lipid A with 4, 5 or 6 acylated chains and is manufactured by Ribi Immunochem, Montana A preferred form is disclosed in International Patent Application 92/116556.

Suitable compositions of the invention are those wherein liposomes are initially prepared without MPL, and MPL is then added, preferably as 100 nm particles. The MPL is therefore not contained within the vesicle membrane (known as MPL out). Compositions where the MPL is contained within the vesicle membrane (known as MPL in) also form an aspect of the invention. The antigen can be contained within the vesicle membrane or contained outside the vesicle membrane. Preferably soluble antigens are outside and hydrophobic or lipidated antigens are either contained inside or outside the membrane.

Often the vaccines of the invention will not require any specific carrier and be formulated in an aqueous or other pharmaceutically acceptable buffer. In some cases it may be advantageous that the vaccines of the present invention will further contain alum or be presented in an oil in water emulsion, or other suitable vehicle, such as for example, liposomes, microspheres or encapsulated antigen particles.

Preferably the vaccine formulations will contain an antigen or antigenic composition capable of eliciting an immune response against a human or animal pathogen. Antigen or antigenic compositions known in the art can be used in the compositions of the invention, including polysaccharide antigens, antigen or antigenic compositions derived from HIV-1, (such as gp 120 or gp 160), any of Feline Immunodeficiency virus, human or animal herpes viruses, such as gD or derivatives thereof or Immediate Early protein such as ICP27 from HSV1 or HSV2, cytomegalovirus (especially human) (such as gB or derivatives thereof), Varicella Zoster Virus (such as gpI, II or III), or from a hepatitis virus such as hepatitis B virus for example Hepatitis B Surface antigen or a derivative thereof, hepatitis A virus, hepatitis C virus and hepatitis E virus, or from other viral pathogens, such as Respiratory Syncytial virus (for example HSRV F and G proteins or immunogenic fragments thereof disclosed in U.S. Pat. No. 5,149,650 or chimeric polypeptides containing immunogenic fragments from HSRV proteins F and G, eg FG glycoprotein disclosed in U.S. Pat. No. 5,194,595), antigens derived from meningitis strains such as meningitis A, B and C, Streptoccococcus Pneumonia, human papilloma virus, Influenza virus, Haemophilus Influenza B (Hib), Epstein Barr Virus (EBV), or derived from bacterial pathogens such as Salmonella, Neisseria, Borrelia (for example OspA or OspB or derivatives thereof), or Chlamydia, or Borderella for example P.69, PT and FRA, or derived from parasites such as plasmodium or toxoplasma.

HSV Glycoprotein D (gD) or derivatives thereof is a preferred vaccine antigen. It is located on the viral membrane, and is also found in the cytoplasm of infected cells (Eisenberg R. J. et al; *J of Virol* 1980 35 428–435). It comprises 393 amino acids including a signal peptide and has a molecular weight of approximately 60 kD. Of all the HSV envelope glycoproteins this is probably the best characterised (Cohen et al *J. Virology* 60 157–166). In vivo it is known to play a central role in viral attachment to cell membranes. Moreover, glycoprotein D has been shown to be able to elicit neutralising antibodies in vivo and protect animals from lethal challenge. A truncated form of the gD molecule is devoid of the C terminal anchor region and can be produced in mammalian cells as a soluble protein which is exported into the cell culture supernatant. Such soluble forms of gD are preferred. The production of truncated forms of gD is described in EP 0 139 417. Preferably the gD is derived from HSV-2. An embodiment of the invention is a truncated HSV-2 glycoprotein D of 308 amino acids which comprises amino acids 1 through 306 naturally occuring glycoprotein with the addition Asparagine and Glutamine at the C terminal end of the truncated protein devoid of its membrane anchor region. This form of the protein includes the signal peptide which is cleaved to allow for the manure soluble 283 amino acid protein to be secreted from a host cell.

In another aspect of the invention, Hepatitis B surface antigen is a preferred vaccine antigen.

As used herein the expression 'Hepatitis B surface antigen' or 'HBsAg' includes any HBsAg antigen or fragment thereof displaying the antigenicity of HBV surface antigen. It will be understood that in addition to the 226 amino acid sequence of the HBsAg antigen (see Tiollais et al, *Nature*, 317, 489 (1985) and references therein) HBsAg as herein described may, if desired, contain all or part of a pre-S sequence as described in the above references and in EP-A-0 278 940. In particular the HBsAg may comprise a polypeptide comprising an amino acid sequence comprising residues 12–52 followed by residues 133–145 followed by residues 175–400 of the L-protein of HBsAg relative to the open reading frame on a Hepatitis B virus of ad serotype (this polypeptide is referred to as L*; see EP 0 414 374). HBsAg within the scope of the invention may also include the pre-S1-preS2-S polypeptide described in EP 0 198 474 (Endotronics) or close analogues thereof such as those described in EP 0 304 578 (Mc Cormick and Jones). HBsAg as herein described can also refer to mutants, for example the 'escape mutant' described in WO 91/14703 or European Patent Application Number 0 511 855A1, especially HBsAg wherein the amino acid substitution at position 145 is to arginine from glycine.

Normally the HBsAg will be in particle form. The particles may comprise for example S protein alone or may be composite particles, for example (L*,S) where L* is as defined above and S denotes the S-protein of HBsAg. The said particle is advantageously in the form in which it is expressed in yeast.

The preparation of hepatitis B surface antigen S-protein is well documented See for example, Harford et al (1983) in *Develop. Biol. Standard* 54, page 125, Gregg et al (1987) in *Biotechnology*, 5, page 479, EP 0 226 846, EP 0 299 108 and references therein.

The formulations within the scope of the invention may also contain an anti-tumour antigen and be useful for immunotherapeutically treating cancers.

Vaccine preparation is generally described in New Trends and Developments in Vaccines, edited by Voller et al., University Park Press, Baltimore, Md., U.S.A. 1978. Encapsulation within liposomes is described, for example, by Fullenon, U.S. Pat. No. 4,235,877. Conjugation of proteins to macromolecules is disclosed, for example, by Likhite, U.S. Pat. No. 4,372,945 and by Armor et al., U.S. Pat. 4,474,757.

The amount of protein in each vaccine dose is selected as an amount which induces an immunoprotective response without significant, adverse side effects in typical vaccinees. Such amount will vary depending upon which specific immunogen is employed and how it is presented. Generally, it is expected that each dose will comprise 1–1000 mcg of protein, preferably 2–100 mcg, most preferably 4–40 mcg. An optimal amount for a particular vaccine can be ascertained by standard studies involving observation of appropriate immune responses in subjects. Following an initial vaccination, subjects may receive one or several booster immunisation adequately spaced.

The formulations of the present invention maybe used for both prophylatic and therapeutic purposes.

Accordingly in a further aspect, the invention therefore provides use of a vaccine of the invention for the treatment of human patients. The invention provides a method of treatment comprising administering an effective amount of a vaccine of the present invention to a patient. In particular, the invention provides a method of treating viral, bacterial, parasitic infections or cancer which comprises administering an effective amount of a vaccine of the present invention to a patient.

The following examples and data illustrates the invention.

EXAMPLES 1.1 Method of preparation of liposomes:

A mixture of lipid (such as phosphatidylcholine either from egg-yolk or synthetic) and cholesterol in organic solvent, is dried down under vacuum (or alternatively under a stream of inert gas). An aqueous solution (such as phosphate buffered saline) is then added, and the vessel agitated until all the lipid is in suspension. This suspension is then microfluidised until the liposome size is reduced to 100 nm, and then sterile filtered through a 0.2 μm filter. Extrusion or sonication could replace this step. Typically the cholesterol:phosphatidylcholine ratio is 1:4 (w/w), and the aqueous solution is added to give a final cholesterol concentration of 5 to 50 mg/ml. If MPL in organic solution is added to the lipid in organic solution the final liposomes contain MPL in the membrane (referred to as MPL in). The liposomes have a defined size of 100 nm and are referred to as SUV (for small unilamelar vesicles). If this solution is repeatedly frozen and thawed the vesicles fuse to form large multilamellar structures (MLV) of size ranging from 500 mm to 15 μm. The liposomes by themselves are stable over time and have no fusogenic capacity.

1.2 Formulation procedure:

QS21 in aqueous solution is added to the liposomes. This mixture is then added to the antigen solution which may if desired contain MPL in the form of 100 nm particles.

1.3 The lytic activity of QS21 is inhibited by liposomes containing cholesterol.

When QS21 is added to erythrocytes, they lyse them releasing hemoglobin. This lytic activity can also be measured using liposomes which contain cholesterol in their membrane and an entrapped fluorescent dye, carboxyfluorescein—as the liposomes are lysed the dye is released which can be monitored by fluorescence spectroscopy. If the fluorescent liposomes do not contain cholesterol in their membrane no lysis of the liposomes is observed.

If the QS21 is incubated with liposomes containing cholesterol prior to adding it to erythrocytes, the lysis of the erythrocytes is diminished depending on the ratio of cholesterol to QS21. If a 1:1 ratio is used no lytic activity is detected. If the liposomes do not contain cholesterol inhibition of lysis requires a one thousand fold excess of phospholipid over QS21.

Figure 1:
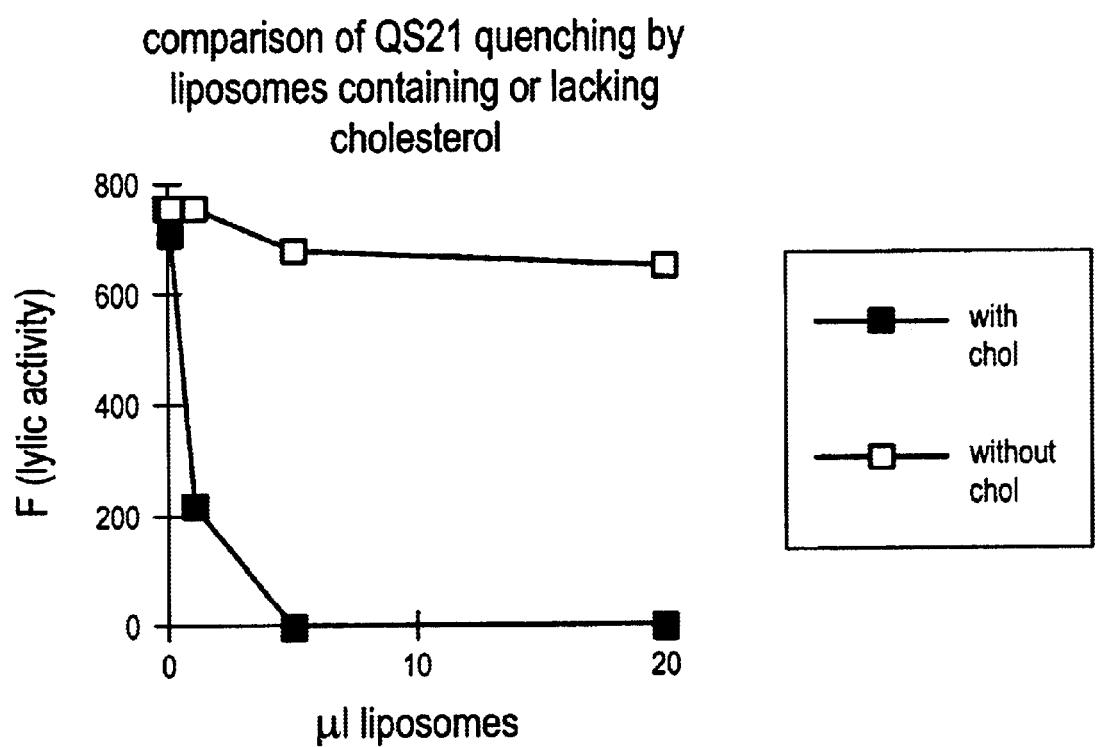
FIG. 1 is comparison of QS21 quenching by liposomes containing or lacking cholesterol.

The same holds true using fluorescent liposomes to measure the lytic activity. In FIG. 1, the lytic activity of 4 μg of QS21 treated with liposomes lacking cholesterol (1 mg eggyolk lecithin per ml) or containing cholesterol (1 mg lecithin, 500 μg cholesterol per ml) was measured by fluorescence.

The data shows that QS21 associates in a specific manner with cholesterol in a membrane, thus causing lysis (of cells or fluorescent liposomes). If the QS21 first associates with cholesterol in liposomes it is no longer lyric towards cells or other liposomes. This requires a minimum ratio of 0.5:1 chol:QS21(w/w).

Cholesterol is insoluble in aqueous solutions and does not form a stable suspension. In the presence of phospholipids the cholesterol resides within the phospholipid bilayer which can form a stable suspension of vesicles called liposomes. To avoid the requirement to add phospholipids a soluble derivative was tried. Polyoxyethanyl-cholesterol sebacate is soluble in water at 60 mg/ml however even at a 2000 fold excess (w/w) over QS21 no reduction in the lytic activity of QS21 was detected.

1.4 Increased stability of QS21 by liposomes containing cholesterol.

Figure 2:
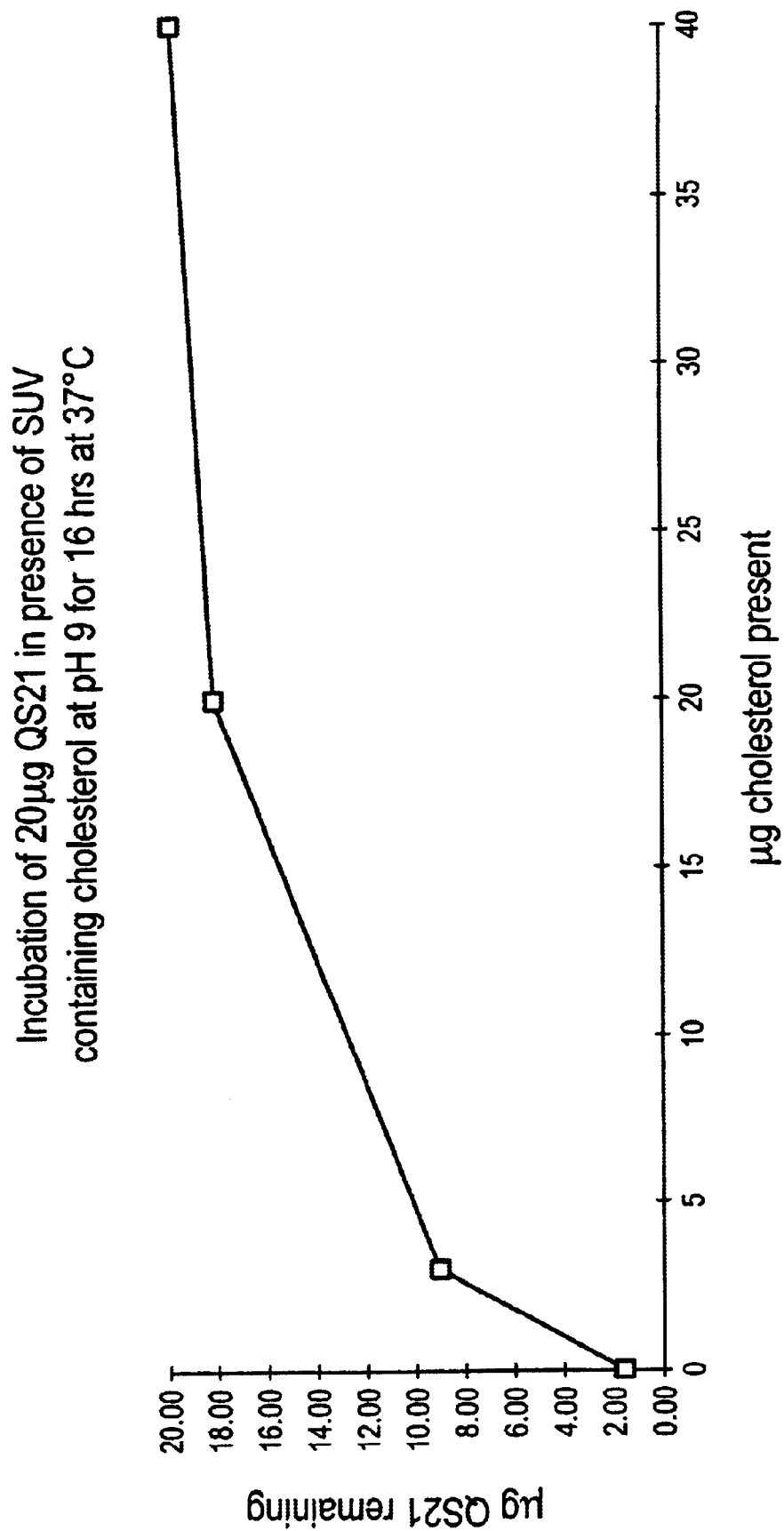
FIG. 2 shows incubation of 20 ug QS21 in presence of SUV containing cholesterol at pH 9 for 16 hrs at 37° C.

QS21 is very susceptible to hydrolysis at a pH above 7. This hydrolysis can be monitored by measuring the decrease in the peak corresponding to QS21 on reverse-phase HPLC. For example, FIG. 2 shows that at pH 9 and at a temperature of 37° C., 90% of QS21 is hydrolysed within 16 hours. If liposomes containing cholesterol are added to the QS21 at a ratio of 2:1 (chol:QS21 w/w) no hydrolysis of the QS21 is detected under the same conditions. If the ratio is 1:1 10% of the QS21 is degraded.

It is concluded that when QS21 associates with liposomes containing cholesterol it becomes much less susceptible to base-mediated hydrolysis. The hydrolysis product is described as having no adjuvant activity when given parentally, hence vaccines containing QS21 have to be formulated at acidic pH and kept at 4° C. to maintain adjuvant composition. The use of liposomes may overcome this requirement 1.5 Reactogenicity studies:

Mice injected in tibialis muscle with 5 μg QS21 (or digitonin) added to increasing quantities of liposomes (expressed in terms of μg cholesterol). Lytic activity is expressed as μg QS21 equivalent, which means that quantity of QS21 required to achieve the same hemolysis as the sample.

Redness, necrosis and toxicity in the muscle at the site of injection were scored visually after sacrificing the mice.

| formulation | lytic activity μg | redness | necrosis | toxicity |
|---|---|---|---|---|
| QS21 +PBS | 5 | +++ | ± | +++ |
| QS21 + 1 μg chol (SUV) | 4 | +++ | + | ++++ |
| QS21 + 5 μg chol (SUV) | 0 | – | – | ± |
| QS21 + 25 μg chol (SUV) | 0 | ± | – | + |
| SUV alone | 0 | – | – | – |
| digitonin | 5 | – | – | ± |
| PBS | 0 | – | – | – |

The data shows that when the lytic activity is abolished by the addition of liposomes containing cholesterol the toxicity due to the QS21 is also abolished.

1.6 Reactogenicity intra-muscularly in rabbits

Values in U.I./L

| Experiment | Formulation | Day0 | hemolysis | Day1 | hemolysis | Day3 | hemolysis |
|---|---|---|---|---|---|---|---|
| Rabbit n°1 | | 1078 | ± | 8650 | | 1523 | |
| Rabbit n°2 | | 1116 | | 4648 | | 1435 | |
| Rabbit n°3 | QS21 50 μg | 660 | | 4819 | | 684 | |
| Rabbit n°4 | | 592 | | 5662 | | 684 | |
| Rabbit n°5 | | 3400 | | 7528 | | 1736 | |
| Mean | | 1369 | | 6261 | | 1212 | |
| SD | | 1160 | | 1757 | | 495 | |
| Rabbit n°6 | | 596 | | 1670 | | 460 | |

-continued

| Experiment | Formulation | Day0 | hemolysis | Day1 | hemolysis | Day3 | hemolysis |
|---|---|---|---|---|---|---|---|
| Rabbit n°7 | | 540 | | 602 | | 594 | |
| Rabbit n°8 | QS21 50 μg | 611 | | 1873 | | 803 | |
| Rabbit n°9 | Chol in SUV 50 μg | 521 | | 507 | | 616 | |
| Rabbit n°10 | (1:1) | 1092 | ± | 787 | | 555 | |
| Mean | | 672 | | 1088 | | 606 | |
| SD | | 238 | | 636 | | 125 | |
| Rabbit n°11 | | 332 | | 344 | | 387 | |
| Rabbit n°12 | | 831 | | 662 | | 694 | |
| Rabbit n°13 | QS21 50 μg | 464 | | 356 | | 519 | |
| Rabbit n°14 | Chol in SUV 150 μg | 528 | | 720 | | 614 | |
| Rabbit n°15 | (1:3) | 1027 | | 568 | | 849 | |
| Mean | | 637 | | 530 | | 613 | |
| SD | | 285 | | 173 | | 175 | |
| Rabbit n°16 | | 540 | | 769 | | 745 | |
| Rabbit n°17 | | 498 | | 404 | | 471 | |
| Rabbit n°18 | QS21 50 μg | 442 | | 717 | | (4535) | |
| Rabbit n°19 | Chol in SUV 250 μg | 822 | | 801 | | 925 | |
| Rabbit n°20 | (1:5) | 3182 | ± | 2410 | | 960 | |
| Mean | | 1097 | | 1020 | | 775 | (1527) |
| SD | | 1175 | | 793 | | 224 | (1692) |
| Rabbit n°21 | | 321 | | 290 | | 378 | |
| Rabbit n°22 | | 660 | | 535 | | 755 | |
| Rabbit n°23 | PBS | 650 | | 603 | | 473 | |
| Rabbit n°24 | | 1395 | | (3545) | | (5749) | |
| Rabbit n°25 | | 429 | ± | 323 | | 263 | |
| Mean | | 691 | | 438 | (1059) | 467 | (1523) |
| SD | | 419 | | 155 | (1396) | 210 | (2369) |

The data shows that the addition of cholesterol-containing liposomes to the formulation significantly reduces the elevation in CPK (creatine phospho kinase) caused by the QS21. Since the CPK increase is a measure of muscle damage this indicates decreased muscle damage and is confirmed by the histopathology.

1.7 Binding of the liposome-QS21 complex to alum.

QS21 was incubated with neutral liposomes containing excess cholesterol as well as radioactive cholesterol and then incubated with alum (Al(OH)$_3$) in PBS. Alone, neither neutral liposomes nor QS21 bind to alum in PBS, yet negatively charged liposomes do. When together however, QS21 and neutral liposomes bind to alum. The supernatant contained neither QS21 (assayed by orcinol test) nor radioactive cholesterol.

This indicates that the QS21 has bound to the liposomes and permits the liposome-QS21 combination to bind to the alum. This may arise from a negative charge being imposed on the liposomes by the QS21, or to an exposure of hydrophobic regions on the liposomes. The results also imply that QS21 does not extract cholesterol from the membrane.

This indicates that compositions of the invention can be used in alum based vaccines.

1.8 Comparison of liposomal QS21/MPL and free QS21+MPL for antibody and CMI induction SUV were prepared by extrusion (EYPC:chol:MPL 20:5:1).

For MPL out, liposomes were prepared without MPL and MPL added as 100 nm. particles QS21 was added prior to antigen. Chol:QS21=5:1 (w/w) MLV were made by freeze-thawing SUV 3× prior to antigen addition. To have the antigen entrapped, the antigen was added to SUV prior to freeze-thawing and QS21 added after freeze-thaw. Antigen encapsulation=5% in, 95% out. -mice (balb/c for gD, B 10BR for RTSs) were injected twice in the footpad. gD is the glycoprotein D from Herpes Simplex virus. RTSs is the Hepatitis B surface antigen (HBsAg) genetically modified to contain an epitope from the Plasmodiium falciparum sporozoit.

| ag = 10 μg RTSs | anti HBsAg Titres 15 days post boost | | |
|---|---|---|---|
| formulation | IgG1 | IgG2a | IgG2b |
| SUV/QS + MPL$_{(out)}$ + Ag | 1175 | 10114 | 71753 |
| MLV/QS + MPL$_{(out)}$ + Ag | 2247 | 11170 | 41755 |
| MLV/QS/MPL$_{(in)}$ + Ag | 969 | 7073 | 18827 |
| MLV/QS/MPL$_{(in)}$/Ag$_{(in)}$ + Ag | 1812 | 2853 | 9393 |
| QS + MPL + Ag | 372 | 9294 | 44457 |
| Ag | <100 | <100 | <100 |
| SUV/QS + MPL$_{(out)}$ | <100 | <100 | <100 |
| MLV/QS/MPL$_{(in)}$ | <100 | <100 | <100 |

| | anti- | CMI | |
|---|---|---|---|
| ag = 20 μg gD formulation | gD IgG | IFN-γ96 hr (pg/ml) | IL2 48 hr pg/ml |
| SUV/QS + MPL$_{(out)}$ + Ag | 2347 | 1572 | 960 |
| SUV/QS/MPL$_{(in)}$ + Ag | 2036 | 1113 | 15 |
| MLV/QS + MPL$_{(out)}$ + Ag | 1578 | 863 | 15 |
| MLV/QS/MPL$_{(in)}$ + Ag | 676 | 373 | 15 |
| MLV/QS/MPL$_{(in)}$/Ag$_{(in)}$ + Ag | 1064 | 715 | 15 |
| QS + MPL + Ag | 1177 | 764 | 15 |
| Ag | <100 | 567 | 44 |
| SUV/QS + MPL$_{(out)}$ | <100 | 181 | 15 |
| MLV/QS/MPL$_{(in)}$ | <100 | 814 | 105 |

The data shows that SUV/QS+MPL(out) induces high antibody titres at least as good as QS21+MPL, as well as inducing IL2 a marker of cell mediated immunity, while quenching QS21 reactogenicity.

Additional results from a second experiment comparing QS21 and QS21 in the presence of cholesterol (SUV) in balb/c mice with HSV gD as antigen are shown below:

|  |  | IgG 7 post II (GMT) | IgG 14 post II (GMT) | Isotypes 7 days post II | | | | | |
|---|---|---|---|---|---|---|---|---|---|
|  |  |  |  | IgG1 | | IgG2a | | IgG2b | |
| Formulation | antigen |  |  | µg/ml | % | µg/ml | % | µg/ml | % |
| SUV/QS21 + MPL out | gD (5 µg) | 20290 | 16343 | 331 | 26 | 716 | 56 | 222 | 17 |
| SUV/QS21/MPL in | gD (5 µg) | 12566 | 10731 | 418 | 44 | 412 | 44 | 111 | 12 |
| QS21 + MPL | gD (5 µg) | 10504 | 10168 | 200 | 34 | 285 | 48 | 107 | 18 |
| SUV/QS21 + MPL out | none | 0 | 0 | 0 | 0 | 0 | 0 | 0 | 0 |
| QS21 | gD (5 µg) | 3468 | 4132 | 156 | 66 | 67 | 28 | 14 | 6 |
| SUV/QS21 | gD (5 µg) | 11253 | 11589 | 484 | 57 | 304 | 36 | 65 | 8 |

1.9 Comparison of gp120 plus liposomal MPL/QS21 with free MPL/QS21

Liposomes=SUV containing MPL in the membrane Chol:QS21=6:1

Response was tested two weeks after one immunisation

| formulation | proliftn | IFN-g ng/ml | IL2 pg/ml | IL5 pg/ml |
|---|---|---|---|---|
| SUV/MPL/QS21 + Ag | 12606 | 16.6 | 59 | 476 |
| MPL + QS21 + Ag | 16726 | 15.8 | 60 | 404 |

After second immunisation:

| formulation | proliftn | IFN-g ng/ml | IL4 pg/ml | IL5 pg/ml |
|---|---|---|---|---|
| SUV/MPL/QS21 + Ag | 12606 | 135 | 0 | 250 |
| MPL + QS21 + Ag | 16726 | 60 | 0 | 500 |

The data shows that QS21 associated with cholesterol-containing liposomes and MPL induces Th1/Th0 response equal to MPL+QS21. At this ratio of cholesterol to QS21, QS21 is non-toxic in rabbits (by CPK).

Figure 3:
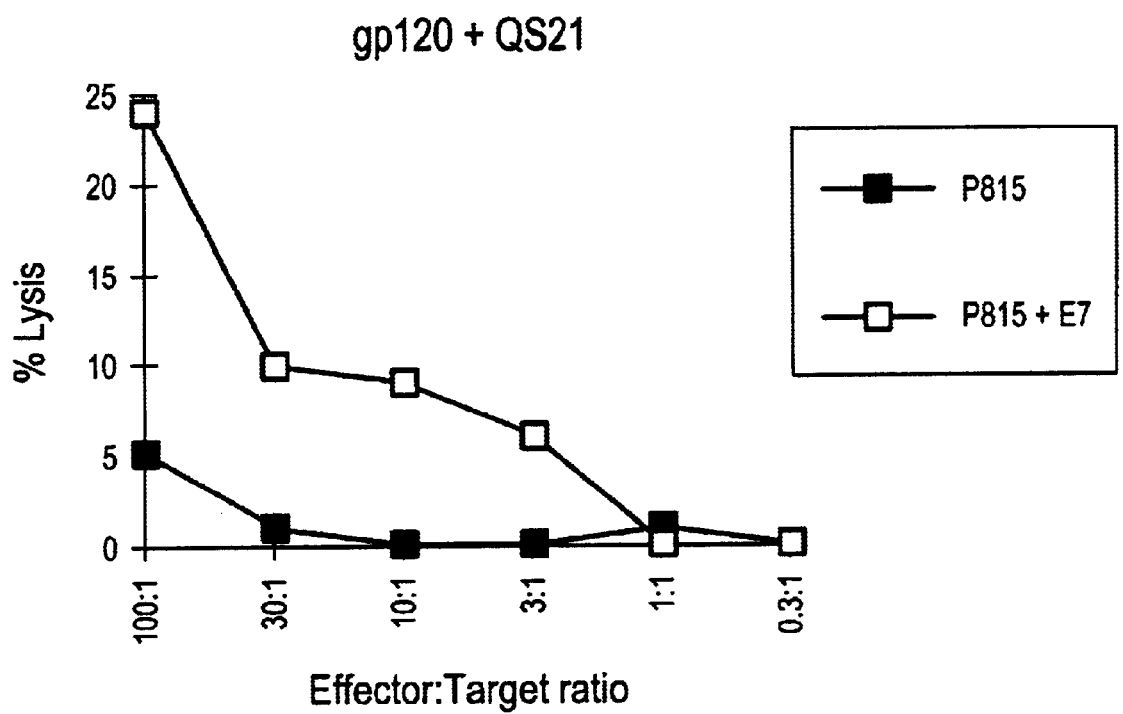
FIG. 3 shows balb/c mice were immunized intra-footpad with gp 120 in the presence of QS21. The cytotoxic T-lymphocyte activity in spleen cells was measured.
Figure 4:
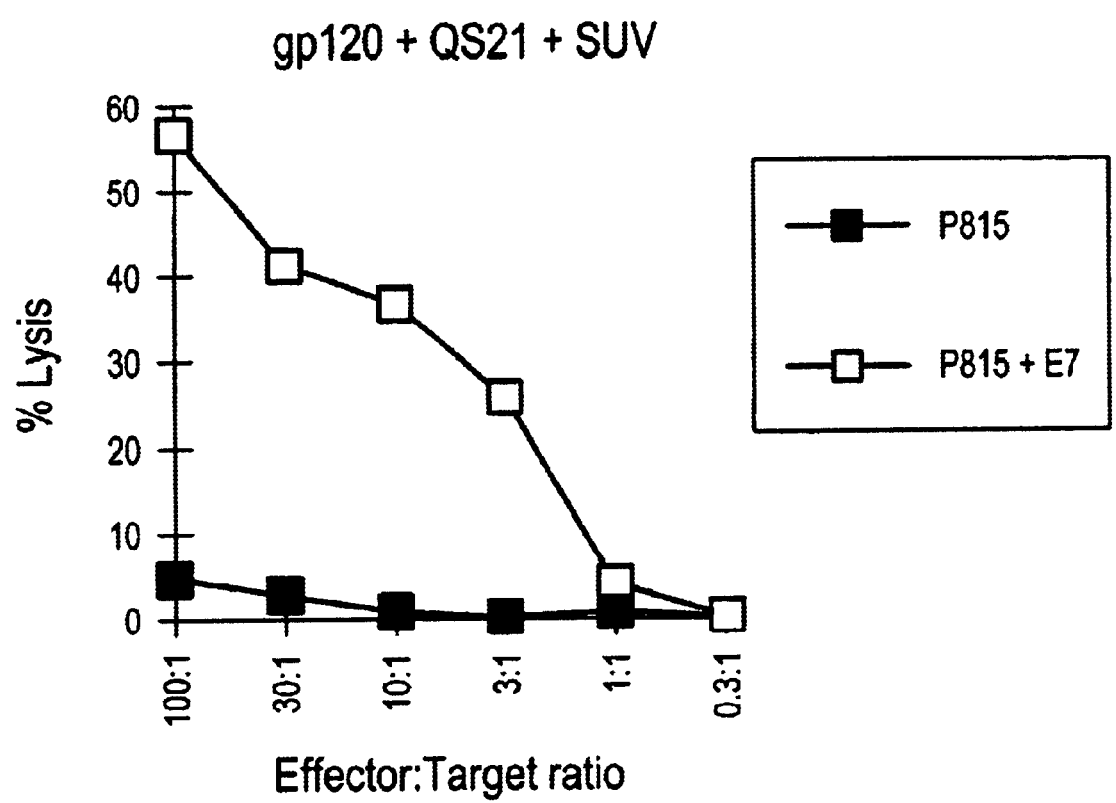
FIG. 4 shows balb/c mice were immunized intra-footpad with gp 120 in the presence of QS21+SUV containing choloesterol. The cytotoxic T-lymphocyte activity in spleen cells was measured.

In a second experiment balb/c mice were immunised intra-footpad with gp120 in the presence of QS21 (see FIG. 3) or QS21+SUV containing cholesterol (see FIG. 4). The cytotoxic T-lymphocyte activity in spleen cells was measured.

This demonstration that QS21 alone indicates CTL activity, and that QS21 in the presence of liposomes containing cholesterol induces CTL activity at least as good as, or better than, QS21 alone.

2. Vaccines 2.1 Formulation of HBsAg L*,S particles

HBsAg L*,S particles may be formulated as follows:

This of HBsAg L*,S particles/dose are incubated 1 h. at room temperature under agitation. The volume is adjusted using water for injection and a PBS solution and completed to a final volume of 70 µl/dose with an aqueous solution of QS21 (10 µg/dose). pH is kept at 7±0.5.

Similar formulations may be prepared using 1 and 50 µg of HBsAg L*,S and also using the BsAg S antigen.

These formulations may be tested in the Woodchuck surrogate therapeutic model using Woodchuck HBV antigens as a model.

Woodchuck model

DQ QS21 (i.e. QS21/cholesterol or quenched QS21) may be tested in the woodchuck therapeutic model where animals are chronically infected with the virus. Specific woodchuck hepatitis virus vaccine may be add mixed with QS21 as such or DQ and with or without MPL and administered to the animals every months for 6 months. Effectiveness of the vaccine may be assess through viral DNA clearance.

2.2 Guinea Pig Model (HSV)

2.2.1 Prophylactic model

Groups of 12 female Hartley guinea pigs were either injected intramuscularly on day 0 and day 28 with the following formulations:

1st experiment:
 gD 5 µg+QS21 50 µg+SUV containing 50 µg cholesterol
 gD 5 µg+QS21 100 µg+SUV containing 100 µg cholesterol
 gD 5 µg+QS21 50 µg+SUV containing 250 µg cholesterol
 gD 5 µg+QS21 50 µg 2nd experiment
 gD 5 µg+MPL 12.5 µg+QS21 12.5 µg+SUV containing 62.5 µg cholesterol, or left untreated.

The animals were bled at 14 and 28 days after the second immunisation, and the sera tested for their gd-specific ELISA antibody titres.

Animals were then challenged intravaginally with $10^5$ pfu HSV-2 MS strain. They were scored daily from day 4 to 12 for evaluation of primary herpetic lesions. Scoring was as follows:

Vaginal lesions:
 bleeding=0.5
 redness for one or 2 days without bleeding=0.5
 redness and bleeding for a day=1
 redness without bleeding lasting at least 3 days=1
External herpetic vesicles:
 <4 small vesicles=2
 >=4 small vesicles or one big vesicle 4>=4 large lesions
  8 fusing large lesions=16
 fusing large lesions on all external genital area=32.

The results are shown in the table below:

| | | Prophylactic Model | | | | | | | |
|---|---|---|---|---|---|---|---|---|---|
| | | | | | PRIMARY DISEASE | | | | |
| | | Ab titres (GMT) | | Animal without lesion % | Vaginal lesions incidence % | External lesions incidence % | PI Index** reduction vs Control | Lesion severity* Median | n |
| | | ELISA day 14 post II | NEUTRA day 28 post II | | | | | | |
| | | day 28 post II | | | | | | | |
| n | FORMULATION | | | | | | | | |
| | Experiment 1 (chol refers to SUV containing cholesterol) | | | | | | | | |
| 12 | gD/QS21 50 μg | | | 50 | 33 | 17 | 73 | 93% | 1.50 | 6 |
| 11 | gD/QS21 50 μg-chol 1/5 | | | 64 | 18 | 18 | 67 | 93% | 2.50 | 4 |
| 12 | gD/QS21 50 μg-chol 1/1 | | | 100 | 0 | 0 | 0 | 100% | — | — |
| 12 | gD/QS21 50 μg-chol 1/1 | | | 50 | 33 | 17 | 54 | 95% | 0.75 | 6 |
| 12 | UNTREATED | | | 25 | 0 | 75 | 996 | — | 55.00 | 9 |
| | Experiment 2 | | | | | | | | |
| 12 | gD/QS21/SUV/MPL | 47006 | 31574 | 449 | 58.33 | 33.33 | 8.33 | 37.50 | 94% | 1.00 | 5 |
| 12 | UNTREATED | <400 | <400 | <50 | 16.67 | 8.33 | 75.00 | 587.50 | — | 11.50 | 10 |

*Sum of the lesion scores for the days 4 to 12 post-infection (animals without lesion are not considered). Lesion scores: no lesion (0), vaginal lesions (0.5 or 1), external skin vesicles (2, 4, 8 or 16)
**Primary infection index = SUM (Max. score i) × (Incidence %); with i = 0, 0.5, 1, 2, 4, 8 or 16

The table and graph show that in the prophylactic model, a very high level of protection against primary disease was induced upon immunisation with gD/MPL/QS21/SUV. Both the incidence of external lesions and the lesion severity appeared highly reduced in the group of animals immunised with gD/MPL/QS21/SUV.

2.2.2 Therapeutic Model

In the therapeutic model, female Hartley guinea pigs were first challenged with $10^5$ pfu HSV-2 MS strain. Animals with herpetic lesions were then randomly allotted to groups of 16.

On day 21 and day 42, they were either immunised with one of the following gD+MPL 50 μg+QS21 50 μg+SUV containing 250 μg cholesterol, gD+Al(OH)$_3$+MPL 50 μg+QS21 50 μg,+SUV containing 250 μg cholesterol or left untreated They were monitored daily from day 22 to 75 for evaluation of recurrent disease. Scoring was as described for the prophylactic model. The results are shown in the table and graph below:

| | | Therapeutic Model | | | | | |
|---|---|---|---|---|---|---|---|
| | | SEVERITY* | | DURATION** | | EPISODE NBER*** | |
| n | FORMULATIONS | Median | % reduction vs Control | Median | % reduction vs Control | Median | % reduction vs Control |
| 16 | gD + MPL + QS21 + SUV | 9.00 | 43% | 7.00 | 18% | 3.00 | 14% |
| 15 | gD + Al(OH)3 + MPL + QS21 + SUV | 8.50 | 46% | 7.00 | 18% | 3.00 | 14% |
| 16 | Untreated | 15.75 | — | 8.50 | — | 3.50 | — |

*Sum of the lesion scores for the days 22 to 75 post-infection.
**Total days animals experienced recurrent lesions for the days 22 to 75 post infection
***Recurrence episode number for the days 22 to 75 post infection. One episode is preceded and followed by a day without lesion and characterized by at least two days with erythema (score = 0.5) or one day with external vesicle (score >= 2) Immunotherapeutical treatment performed on days 21 and 42.
The results show that good levels of protection were also induced in the therapeutic model of HSV-2 infection. Immunization with gD/MPL/QS21/SUV with or without Alum had a marked effect on the median severity of recurrent disease. It also slightly reduced episode number and duration (see Table).

What is claimed is:

1. An adjuvant composition comprising a sterol and a substantially pure preparation of QS21, characterized in that the adjuvant composition is in the form of an ISCOM.

2. An adjuvant composition according to claim 1, wherein the QS21 is at least 90% pure.

3. An adjuvant composition according to claim 1, wherein the QS21 is at least 95% pure.

4. An adjuvant composition according to claim 1, wherein the QS21 is at least 98% pure.

* * * * *